US012239789B2

(12) United States Patent
Lucio

(10) Patent No.: US 12,239,789 B2
(45) Date of Patent: *Mar. 4, 2025

(54) NASAL CANNULA WITHOUT NOSTRIL PRONGS

(71) Applicant: 3B Medical, Inc., Winter Haven, FL (US)

(72) Inventor: Albert A. Lucio, Haines City, FL (US)

(73) Assignee: 3B Medical, Inc., Dublin, OH (US)

( * ) Notice: Subject to any disclaimer, the term of this patent is extended or adjusted under 35 U.S.C. 154(b) by 999 days.

This patent is subject to a terminal disclaimer.

(21) Appl. No.: 17/217,073

(22) Filed: Mar. 30, 2021

(65) Prior Publication Data

US 2021/0402125 A1 Dec. 30, 2021

Related U.S. Application Data

(63) Continuation of application No. 16/910,155, filed on Jun. 24, 2020, now Pat. No. 10,987,480.

(51) Int. Cl.
*A61M 16/06* (2006.01)
(52) U.S. Cl.
CPC . *A61M 16/0672* (2014.02); *A61M 2202/0208* (2013.01); *A61M 2209/088* (2013.01)
(58) Field of Classification Search
CPC ............... A41D 13/11; A41D 13/1153; A41D 13/1184; A42B 1/046; A61F 9/029; A61M 16/00; A61M 16/0003; A61M 16/0051; A61M 16/0057; A61M 16/0063; A61M 16/0066; A61M 16/0069; A61M 16/024; A61M 16/06; A61M 16/0605; A61M 16/0611; A61M 16/0616; A61M 16/0622; A61M 16/0633; A61M 16/065; A61M 16/0655; A61M 16/0666; A61M 16/0672;

(Continued)

(56) References Cited

U.S. PATENT DOCUMENTS 2,691,800 A 11/1954 Caldwell
2,693,800 A 11/1954 Caldwell (Continued)

OTHER PUBLICATIONS

3B Mask line up, 3B Medical, Youtube, [Posted on Mar. 26, 2019], [Site visited Aug. 20, 2021], Seen at URL: https://www.youtube.com/ watch?v=pf-rGz602WQ (Year: 2019).

(Continued)

*Primary Examiner* — Annette Dixon
(74) *Attorney, Agent, or Firm* — Carlson, Gaskey & Olds, P.C.

(57) ABSTRACT

This disclosure relates to a nasal cannula without nostril prongs. The nasal cannula may be used together with an oxygen delivery system, such as a portable oxygen concentrator, or another type of breathing device such as a continuous positive airway pressure (CPAP) machine. In an example, a nasal cannula includes a tube configured to connect to an oxygen supply, and a fitting configured to connect to the tube. The fitting includes a single discharge port having a first section configured to be situated inferior to a first nostril of a user and a second section configured to be situated inferior to a second nostril of the user. Further, the fitting does not include nostril prongs. Because the fitting does not include nostril prongs, patient comfort is dramatically increased relative to prior designs.

18 Claims, 5 Drawing Sheets

(58) Field of Classification Search
CPC .......... A61M 16/0677; A61M 16/0683; A61M 16/0694; A61M 16/08; A61M 16/0816; A61M 16/0825; A61M 16/0833; A61M 16/085; A61M 16/0858; A61M 16/0875; A61M 16/0883; A61M 16/101; A61M 16/1045; A61M 16/125; A61M 16/127; A61M 16/16; A61M 16/161; A61M 16/20; A61M 16/208; A61M 2016/0021; A61M 2016/0024; A61M 2016/0027; A61M 2016/003; A61M 2016/0661; A61M 2016/1025; A61M 2025/0059; A61M 2202/0007; A61M 2202/0014; A61M 2202/0085; A61M 2202/0208; A61M 2202/0225; A61M 2202/03; A61M 2205/02; A61M 2205/0205; A61M 2205/0216; A61M 2205/0238; A61M 2205/0266; A61M 2205/0272; A61M 2205/273; A61M 2205/3561; A61M 2205/42; A61M 2205/583; A61M 2205/588; A61M 2205/59; A61M 2205/8206; A61M 2207/00; A61M 2209/06; A61M 2209/082; A61M 2209/088; A61M 2210/0618; A61M 2210/0625; A61M 2230/42; A61M 2230/432; A61M 2230/63; A61M 39/08; A62B 18/00; A62B 18/003; A62B 18/025; A62B 18/084; B63C 11/205; Y10S 128/26; Y10S 128/91

See application file for complete search history.

(56) References Cited

U.S. PATENT DOCUMENTS

| | | | |
|---|---|---|---|
| 3,529,584 A | 9/1970 | Charnley | |
| 3,682,171 A | 8/1972 | Dali et al. | |
| 4,216,769 A | 8/1980 | Grimes | |
| 4,273,124 A | 6/1981 | Zimmerman | |
| 5,526,806 A | 6/1996 | Sansoni | |
| 6,119,694 A | 9/2000 | Correa et al. | |
| 7,007,694 B2 | 3/2006 | Aylsworth et al. | |
| D549,323 S | 8/2007 | Kwok et al. | |
| 7,383,839 B2 | 6/2008 | Porat et al. | |
| D612,934 S | 3/2010 | Prentice et al. | |
| D626,646 S | 11/2010 | Lubke et al. | |
| D627,059 S | 11/2010 | Wood et al. | |
| 8,684,005 B2 | 4/2014 | Jablons | |
| 9,162,034 B2 | 10/2015 | Veliss et al. | |
| 9,180,270 B2 | 11/2015 | Kapust et al. | |
| D745,141 S | 12/2015 | Hung | |
| D757,930 S | 5/2016 | Baecke et al. | |
| 9,393,375 B2 | 7/2016 | Hernandez et al. | |
| 9,474,469 B2 | 10/2016 | Deutsch et al. | |
| D825,053 S | 8/2018 | Ronayne et al. | |
| 10,166,357 B2 | 1/2019 | Veliss et al. | |
| D865,943 S | 11/2019 | Wilson et al. | |
| D878,549 S | 3/2020 | Wilson et al. | |
| D893,013 S | 8/2020 | Higgins et al. | |
| D898,899 S | 10/2020 | Rummery | |
| 10,821,252 B2 | 11/2020 | Chodkowshi | |
| D911,515 S | 2/2021 | Koschany et al. | |
| D916,276 S | 4/2021 | Wilson et al. | |
| 10,987,480 B1 * | 4/2021 | Lucio | A61M 16/0677 |
| 11,266,803 B2 * | 3/2022 | Bell | A61M 16/0666 |
| D983,015 S | 4/2023 | Jasmin et al. | |
| 11,666,722 B2 * | 6/2023 | Lucio | A61M 16/0672 128/207.18 |
| 2002/0092527 A1 | 7/2002 | Wood | |
| 2003/0111081 A1 | 6/2003 | Gupta | |
| 2004/0226566 A1 | 11/2004 | Gunaratnam et al. | |
| 2005/0028822 A1 | 2/2005 | Sleeper et al. | |
| 2006/0266361 A1 | 11/2006 | Hernandez | |
| 2007/0107737 A1 | 5/2007 | Landis et al. | |
| 2008/0060649 A1 * | 3/2008 | Veliss | A61M 16/06 128/207.18 |
| 2010/0113956 A1 | 5/2010 | Curti et al. | |
| 2010/0252042 A1 | 10/2010 | Kapust et al. | |
| 2010/0313898 A1 | 12/2010 | Richard et al. | |
| 2011/0073116 A1 | 3/2011 | Genger et al. | |
| 2011/0094518 A1 | 4/2011 | Cipollone et al. | |
| 2011/0214676 A1 | 9/2011 | Allum et al. | |
| 2012/0111332 A1 | 5/2012 | Gusky et al. | |
| 2014/0094669 A1 | 4/2014 | Jaffe et al. | |
| 2016/0095996 A1 * | 4/2016 | Gusky | A61M 16/0816 128/205.25 |
| 2017/0224942 A1 | 8/2017 | Barbour et al. | |

OTHER PUBLICATIONS

Rio Replacement Nasal Pillow Cushion By 3B Medical, 1800cpap. com, [Post date unknown], [Site visited Aug. 20, 2021], Seen at URL: https://www.1800cpap.com/rio-replacement-nasal-pillow-cushion-by-3b-medical?quantity=1&size=Large&gclid=EAlalQobChMI- 9LC4um_8glVi4rlCh0a%2525E2%252580%2525A6 (Year: 2021).

* cited by examiner

Superior

Inferior

Distal ← → Proximal

Distal ← → Proximal

NASAL CANNULA WITHOUT NOSTRIL PRONGS

RELATED APPLICATION(S)

This application is a continuation of prior U.S. application Ser. No. 16/910,155, filed Jun. 24, 2020, the entirety of which is herein incorporated by reference.

TECHNICAL FIELD

This disclosure relates to a nasal cannula without nostril prongs.

BACKGROUND

In the medical field, oxygen may be supplied to patients to treat a variety of conditions such as heart failure, chronic obstructive pulmonary disease (COPD), or any weakened lung or heart state. Portable oxygen concentrators (POCs) are one known device used in the medical field to supply supplemental oxygen to a patient. POCs take in ambient air, filter it, and deliver a relatively high purity flow of oxygen to the patient. At times, supplemental oxygen is used for purposes outside of the medical field, such as for recreational purposes. Supplemental oxygen may be used to shorten recovery time for exhausted athletes, or may be used at high altitudes to make breathing easier during skiing, mountain biking, or other sporting activities.

SUMMARY

A nasal cannula for an oxygen delivery system according to an exemplary aspect of the present disclosure includes, among other things, a tube configured to connect to an oxygen supply, and a fitting configured to connect to the tube. The fitting includes a single discharge port having a first section configured to be situated inferior to a first nostril of a user and a second section configured to be situated inferior to a second nostril of the user. Further, the fitting does not include nostril prongs.

In a further non-limiting embodiment of the foregoing cannula, the fitting includes a divider located along a centerline of the fitting separating the first section and the second section.

In a further non-limiting embodiment of any of the foregoing cannulas, the divider includes a central portion providing a superior-most portion of the divider, a first wall projecting from the central portion toward a center of the first section and in an inferior direction, and a second wall projecting from the central portion toward a center of the second section and in the inferior direction.

In a further non-limiting embodiment of any of the foregoing cannulas, the fitting does not include a divider such that the first section of the discharge port blends directly into the second section of the discharge port.

In a further non-limiting embodiment of any of the foregoing cannulas, the fitting includes an inclined wall projecting from an apex of a superior surface of the fitting, the apex circumscribes substantially the entire discharge port, and the inclined wall projects from the apex in a direction toward a center of the discharge port and in an inferior direction.

In a further non-limiting embodiment of any of the foregoing cannulas, when the nasal cannula is worn by a user, the fitting is configured to be spaced-apart from a nose of the user.

In a further non-limiting embodiment of any of the foregoing cannulas, a distal-most portion of the inclined wall is notched.

In a further non-limiting embodiment of any of the foregoing cannulas, the fitting includes a main body portion, and the proximal surface of the main body portion is curved.

In a further non-limiting embodiment of any of the foregoing cannulas, the proximal surface of the main body portion is curved following a radius having an origin spaced-apart from the main body portion in the proximal direction.

In a further non-limiting embodiment of any of the foregoing cannulas, the main body portion includes a first prong projecting laterally from a first side of the main body portion, the first prong includes a first inlet port, the first inlet port is fluidly coupled to the discharge port via a first internal passageway, the main body portion includes a second prong projecting laterally from a second side of the main body portion, the second prong includes a second inlet port, and the second inlet port is fluidly coupled to the discharge port via a second internal passageway.

In a further non-limiting embodiment of any of the foregoing cannulas, the main body portion includes an area where the first and second internal passageways meet inferior to the discharge port.

In a further non-limiting embodiment of any of the foregoing cannulas, the first prong is curved following a radius having a first origin superior to the first prong and on the first side of the main body portion, and the second prong is curved following a radius having a second origin superior to the second prong and on the second side of the main body portion.

In a further non-limiting embodiment of any of the foregoing cannulas, the first and second prongs are also curved following a radius having an origin proximal to the fitting.

In a further non-limiting embodiment of any of the foregoing cannulas, a first portion of the tube is configured to fit over the first prong, and a second portion of the tube is configured to fit over the second prong.

In a further non-limiting embodiment of any of the foregoing cannulas, the fitting is integrally formed as a one-piece structure.

In a further non-limiting embodiment of any of the foregoing cannulas, the fitting is provided by an integrally molded piece of plastic.

A system according to an exemplary aspect of the present disclosure includes, among other things, a nasal cannula including a tube and a fitting connected to the tube. The fitting includes a discharge port and the fitting does not include nostril prongs. Further, the fitting includes an inclined wall adjacent the discharge port configured to collect an exhale of a patient. The system also includes an oxygen supply connected to the tube and including a blower and a sensor. The blower is configured to deliver oxygen to the tube.

In a further non-limiting embodiment of the foregoing system, the blower is configured to deliver oxygen to the tube when information from the sensor indicates a change in pressure as low as 0.05 cm $H_2O$.

In a further non-limiting embodiment of any of the foregoing systems, the blower is configured to deliver oxygen to the tube when information from the sensor indicates a change in pressure within a range of as 0.05 cm $H_2O$ and 0.3 cm $H_2O$.

DETAILED DESCRIPTION

This disclosure relates to a nasal cannula without nostril prongs. The nasal cannula may be used together with an oxygen delivery system, such as a portable oxygen concentrator, or another type of breathing device such as a continuous positive airway pressure (CPAP) machine. In an example, a nasal cannula includes a tube configured to connect to an oxygen supply, and a fitting configured to connect to the tube. The fitting includes a single discharge port having a first section configured to be situated inferior to a first nostril of a user and a second section configured to be situated inferior to a second nostril of the user. Further, the fitting does not include nostril prongs. Because the fitting does not include nostril prongs, patient comfort is dramatically increased relative to prior designs. These and other benefits will be appreciated from the below description.

Figure 1:
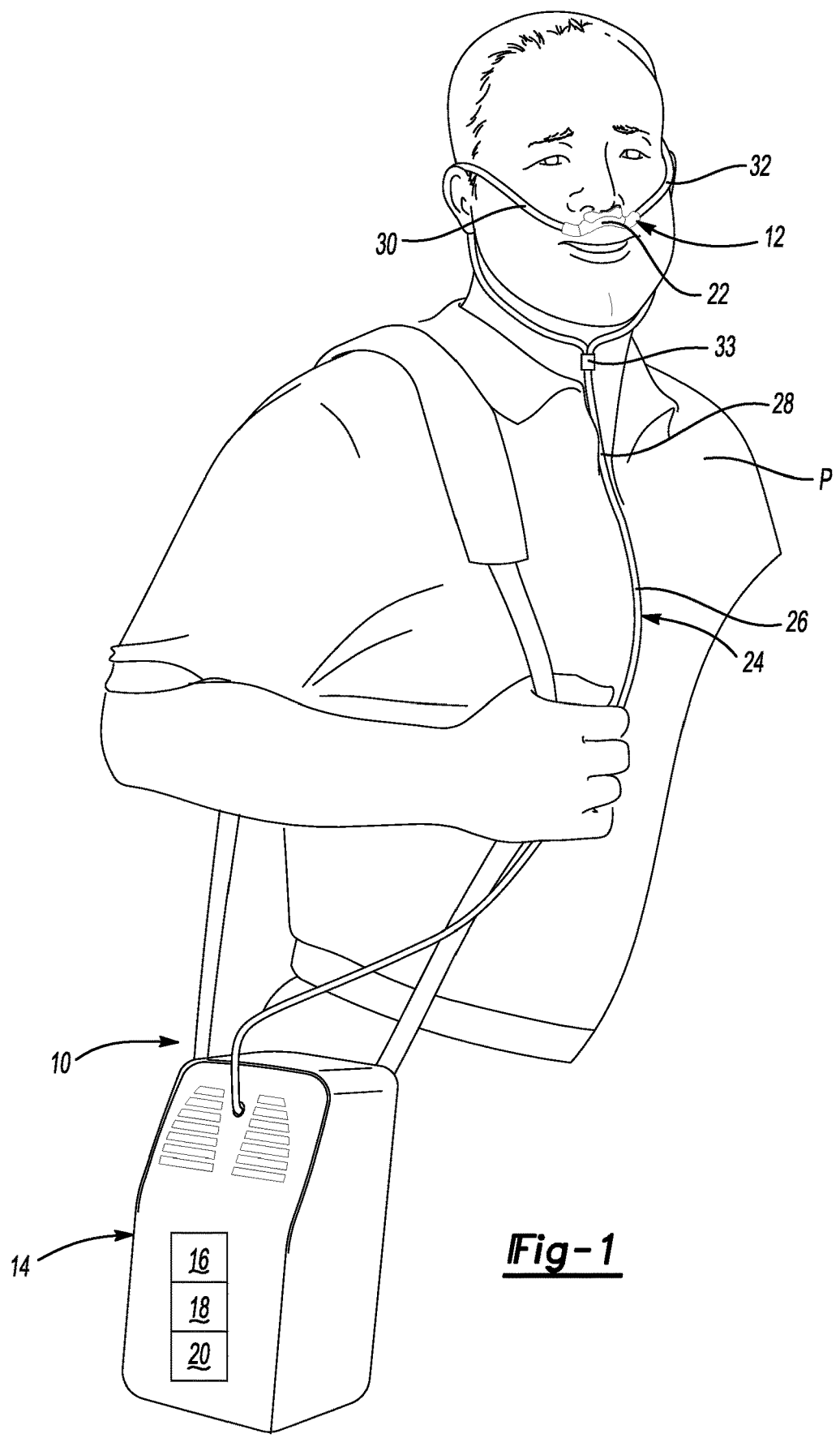
FIG. 1 illustrates, somewhat schematically, an example oxygen delivery system.

FIG. 1 illustrates an example oxygen delivery system 10 ("system 10") with a cannula 12 and an oxygen supply 14. The cannula 12 may be considered a cannula assembly, as it may contain more than one piece, such as a tube and a nasal fitting, among other pieces (such as connectors and collars) as explained below. The oxygen supply 14 is configured to deliver a flow of supplemental oxygen or increased airflow to a patient, or person, P, who is typically a person in need of respiratory help. Alternatively, the patient P could be a person who does not require oxygen for medical purposes but, on the contrary, is an athlete using oxygen for recovery purposes. Further, the patient P could be an athlete engaging in extreme sports, such as skiing or mountain biking, and in particular the patient P could be engaging in such sports at substantially high altitudes, such as in mountainous regions.

In FIG. 1, the oxygen supply 14 is a portable oxygen concentrator (POC). It should be understood that this disclosure extends to cannulas used with other types of oxygen supplies, including oxygen tanks, stationary oxygen concentrators, or a wall connection in a hospital via a flowmeter. This disclosure also extends to cannulas used with other breathing aids, such as a continuous positive airway pressure (CPAP) machine.

The oxygen supply 14 includes an blower 16, such as a pump and/or an air compressor, a sensor 18, and a controller 20, among other structures, such as one or more filters, such as a molecular sieve which separates (i.e., adsorbs) nitrogen from ambient air, and a battery. The blower 16, sensor 18, and controller 20 are shown schematically in FIG. 1. The oxygen supply 14 may use pressure swing adsorption (PSA), vacuum swing adsorption (VSA), or pressure vacuum swing adsorption (PVSA) technology. The oxygen supply 14 may further include a storage chamber, or reservoir. The battery of the oxygen supply 14 may be rechargeable.

Figure 2:
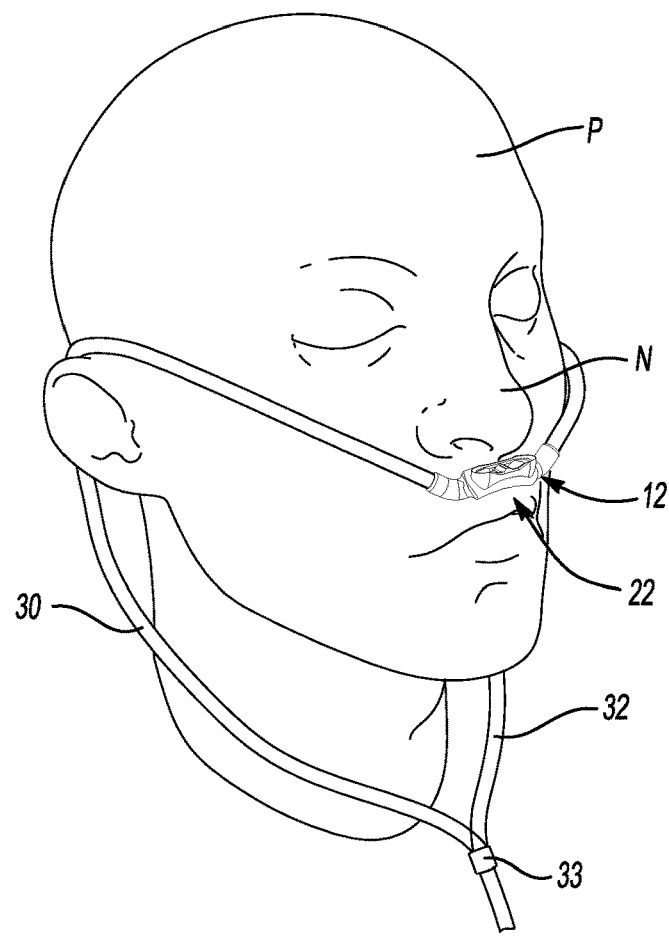
FIG. 2 is a close-up view of a portion of an example cannula relative to a head and neck of a patient.
Figure 3:
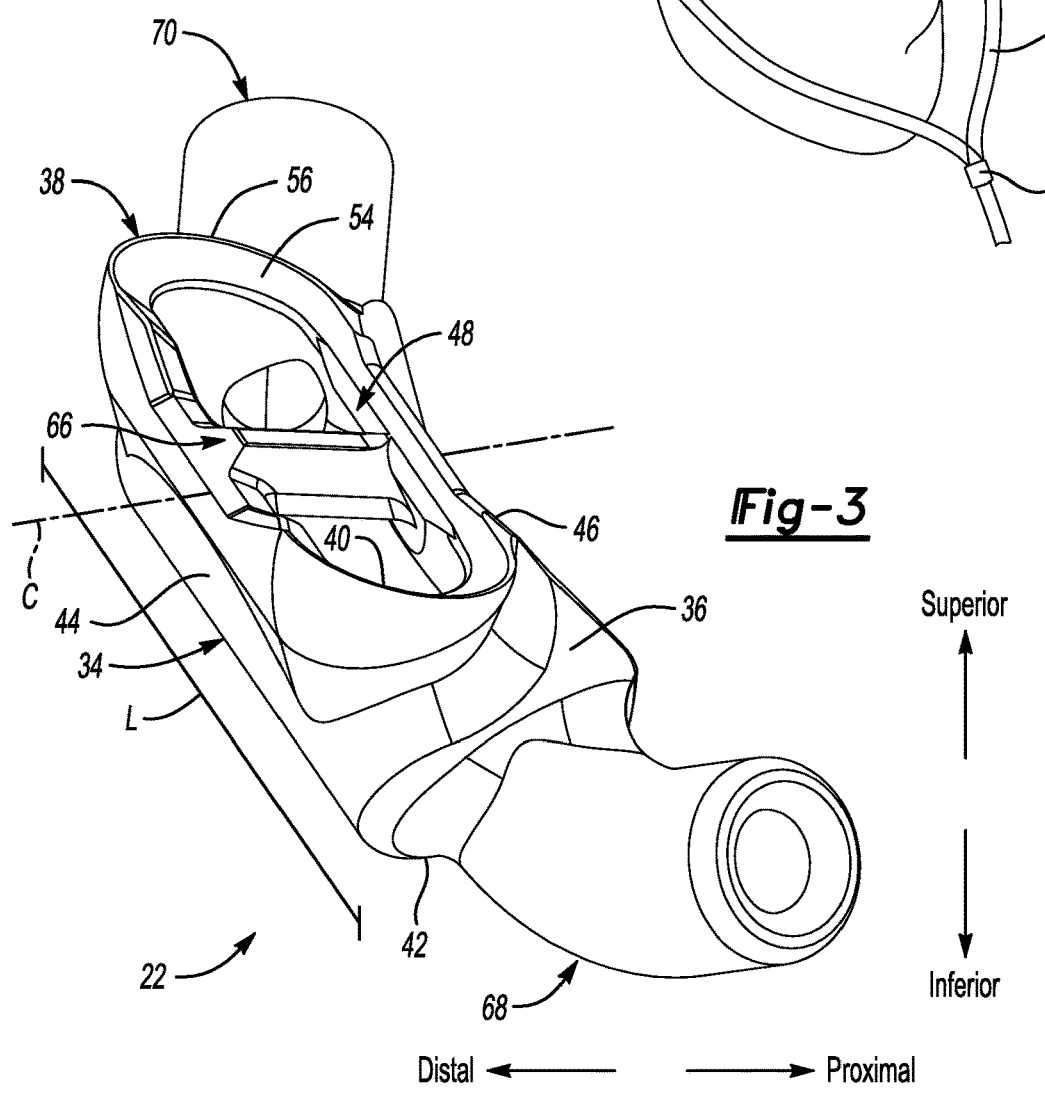
FIG. 3 is a front-perspective view of an example fitting of the example cannula.
Figure 4:
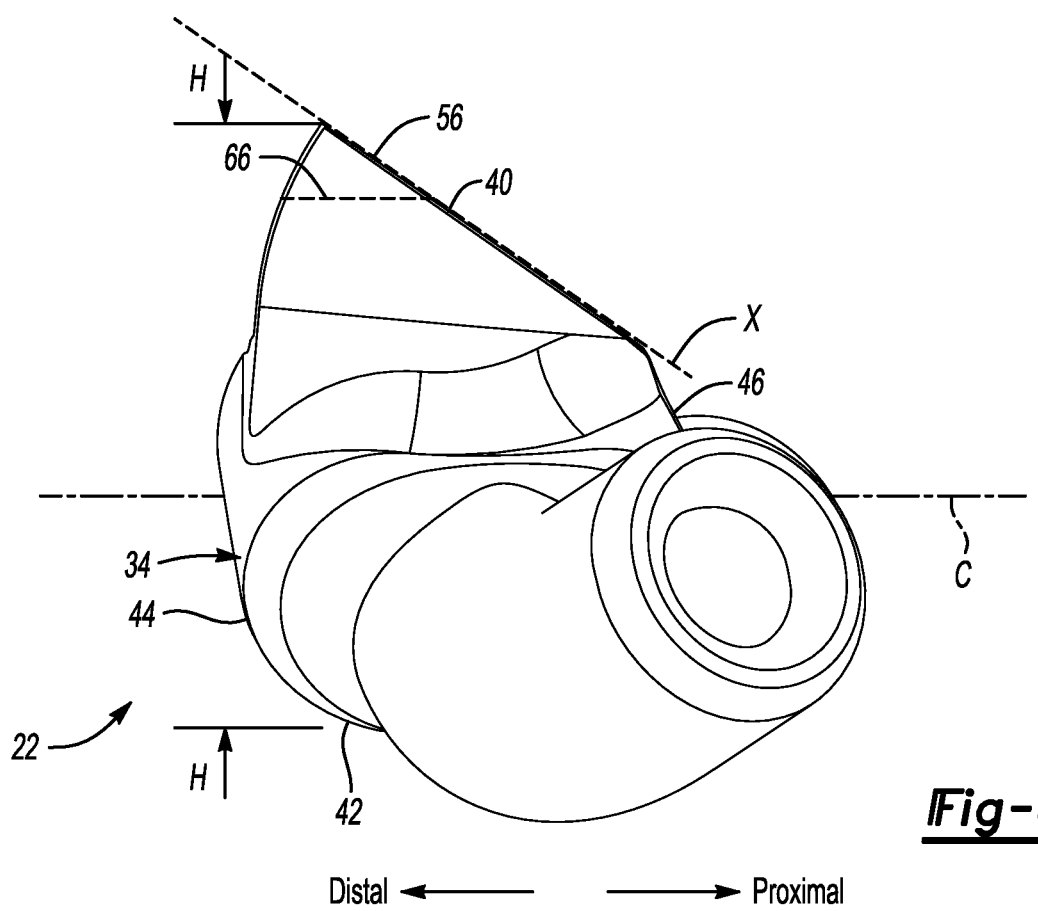
FIG. 4 is a side of view of the example fitting.

The oxygen supply 14 delivers oxygen via the cannula 12 to an interface, which in this example is provided by a nasal fitting 22 ("fitting 22"). The fitting 22 rests beneath a nose of the patient P and delivers oxygen to patient P via their nose N (FIG. 2). The oxygen supply 14 may be a pulse delivery device or a continuous flow device. A continuous flow POC provides a continuous flow of oxygen to the patient. A pulse delivery POC only provides oxygen when the patient P is inhaling. The sensor 18 is configured to generate information (i.e., a signal) indicative of when the patient P is inhaling by detecting a change in pressure. In this sense, the sensor 18 may be considered a pressure sensor. The controller 20 is configured to interpret the signal from the sensor 18 and, when a particular change in pressure is identified, the controller 20 instructs the blower 16 to deliver a pulse of oxygen to the person P. As will be discussed below, the sensor 18 is relatively sensitive compared to traditional sensors, and the controller 20 is configured to instruct the blower 16 to provide a pulse of oxygen when a relatively low change in pressure is met or exceeded.

Ambient air contains about 21% oxygen and about 79% nitrogen and other gases. The oxygen supply 14 compresses the ambient air and filters the nitrogen out of the air, leaving oxygen as the primary gas in the product fluid flow delivered to the user via the fitting 22. The nitrogen is released back to the ambient environment and/or held in the filters. In a typical medical grade POC, the gas delivered to the patient P is around 90-95% oxygen. In other embodiments, such as in POCs for recreational use, a lower oxygen purity is delivered to the patient P. The oxygen supply 14 may include flow control buttons and indicators for breath detection or alerts, and sometimes includes the ability to toggle between a continuous flow and a pulse flow.

The controller 20 may include hardware and/or software, and may be programmed with executable instructions for interfacing with and operating the various components of the oxygen supply 14. In an embodiment, the controller 20 and the sensor 18 are mounted to a common printed circuit board within the oxygen supply 14. It should be understood that the controller 20 could be part of an overall control module. The controller 20 includes a processing unit and non-transitory memory for executing the various control strategies and modes of the oxygen system 10.

In this example, the cannula 12 includes a tube 24 fluidly connecting the oxygen supply 14 to the fitting 22. The tube 24, in this example, includes a main section 26 connected directly to the oxygen supply 14 and extending to a split 28. At the split 28, the tube 24 branches into a first portion 30 and a second portion 32, each of which are connected directly to a respective side of the fitting 22. The first and second portions 30, 32 wrap around opposite ears of the patient P. An adjustable collar 33, which is slidable along the first and second portions 30, 32, is below a chin of the patient P.

The fitting 22 rests below a nose N of the patient, as shown in FIG. 2. In particular, the fitting 22 rests against the face of the patient P, specifically against the philtrum, including the philtral dimple and/or the philtral columns, at a location superior to (e.g., vertically above) the upper lip and inferior to (e.g., vertically below) the base of the nose N.

The fitting 22 does not include nostril prongs, which are found in traditional nasal cannulas and CPAP nasal pillows. Nostril prongs are structures, namely protrusions, which enter into the nostrils of the patient P. In this disclosure, the fitting 22 does not include any such structures that project into the nostrils of the patient P. In fact, in some examples, the fitting 22 is spaced-apart from the nose N of the patient P, and rests against an area superior to the upper lip of the patient P without directly contacting the nose N. In other examples, the columella (i.e., the inferior margin of the septum) of the nose N may contact a superior (i.e., upper) surface of the fitting 22. In either example, no portion of the fitting 22 enters the nostrils of the patient P. Further, in this disclosure, the fitting 22 does not surround the tip of the nose, as is common in some known CPAP masks and CPAP pillows.

FIGS. 3-6 illustrate additional detail of the fitting 22. With joint reference to those figures, the fitting 22 is substantially symmetrical about its centerline C. Specifically, the fitting 22 is symmetrical about a plane containing the centerline C and extending in the superior and inferior directions, labeled in some figures for reference. The fitting 22 includes a main body portion 34 having a length L extending between a first lateral side 36 and a second lateral side 38 of the main body portion 34. In an example, the length L is about 22 mm. The term lateral refers to the lateral direction, which is substantially normal to the centerline C and the inferior and superior directions.

The main body portion 34 also includes a height H (FIG. 4) vertically between a superior (i.e., vertically upper) surface 40 and an inferior (i.e., vertically lower) surface 42. In one example, a ratio between a length L and the height H is about 2.2:1. The height H is 10 mm in an example. The main body portion 34 further includes a width W (FIG. 5) in a direction parallel to the centerline C between a distal (i.e., forward facing) surface 44 and a proximal (i.e., rearward facing) surface 46. A ratio between a length L and the width W is 2.2:1 The width W is 10 mm in an example. The ratio between the width W and height H is 1:1 in an example.

The superior surface 40 includes a single discharge port 48 in this example. In other words, the superior surface 40, and the fitting 22 overall, does not include more than one discharge port 48. Rather, in the embodiment of FIGS. 3-6, the fitting 22 includes a single discharge port 48 having a divider which divides the discharge port 48 into two sections, and in FIG. 7 the fitting 22 includes a single discharge port without a divider. Providing a single discharge port 48, which is larger by area than a nostril prong, for example, makes it easier for the fitting 22 to deliver flow to the nose N of the patient P and to collect exhaled flow from the nose N.

The discharge port 48 is configured to deliver fluid to the nose N of the patient P. In this example, the discharge port 48 is formed in the superior surface 40 of the main body portion 34. The discharge port 48 includes a first section 50 configured to be situated inferior to a first nostril of the patient P, and a second section 52 configured to be situated inferior to a second nostril of the patient P. The discharge port 48 is substantially stadium-shaped when viewed from above. Other shapes come within the scope of this disclosure, however.

An inclined wall 54 is provided adjacent the discharge port 48. The inclined wall 54 projects toward the center of the discharge port 48 and in the inferior direction from an apex 56 defining a superior-most portion of the fitting 22. The apex 56 circumscribes substantially the entire discharge port 48 and lies in a plane X. The plane X is inclined at approximately a 45° angle relative to the distal and proximal directions. The plane X also defines the superior boundary of the discharge port 48. The inclined wall 54 is inclined at an acute, and substantially constant, angle in the inferior direction relative to the plane X about its entire perimeter.

The inclined wall 54 assists in directing exhaled flow from the nostrils of the patient P back into the fitting 22. As such, the inclined wall 54 increases the ease of detecting exhalation, which is particularly relevant in the context of a pulse delivery device. Pulse delivery devices attempt to deliver a pulse of oxygen timed with a patient's inhalation. In an example, the controller 20 uses exhalation to time delivery of the next pulse of oxygen. In particular, when exhalation is detected, the controller 20 instructs the disclosed device to begin readying a pulse of oxygen for the patient's next inhalation. Since the fitting 22 does not include nasal prongs, it can in some circumstances be difficult to capture the airflow from the patient's exhalation. In turn, in those circumstances, it can be difficult to identify when exhalation occurs. The inclined wall 54 ensures that an adequate amount of exhalation airflow is captured, which makes it more likely that the sensor 18 and controller 20 will be able to identify the exhalation and, in turn, that the pulse device will function properly.

The fitting 22 includes a divider 58 located along the centerline C. The divider 58 is spaced inferior to the apex 56. In particular, the divider 58 is spaced inferior to the plane X. The divider 58 separates the first section 50 and the second section 52. The divider 58 is configured to deliver flow to and from the nostrils of the patient P. The divider 58, in this example, includes a central portion 60 providing a superior-most portion of the divider 58, a first wall 62 projecting from the central portion 60 toward the center of the first section 50 and in an inferior direction, and a second wall 64 projecting from the central portion 60 toward the center of the second section 52 and in the inferior direction. The first and second walls 62, 64 blend into the inclined wall 54 in this example. The first and second walls 62, 64 are inclined at the same angle relative to the plane X as the inclined wall 54 in this example. While a divider 58 is present in this embodiment, in other embodiments there is no divider and the first and second sections 50, 52 directly blend into one another, as in FIG. 7. When the divider 58 is present, the dimensions of the divider 58 can be adjusted. In particular, the central portion 60 can have a width of about 5-6 mm to correspond to a width of an average septum and/or columella.

Figure 5:
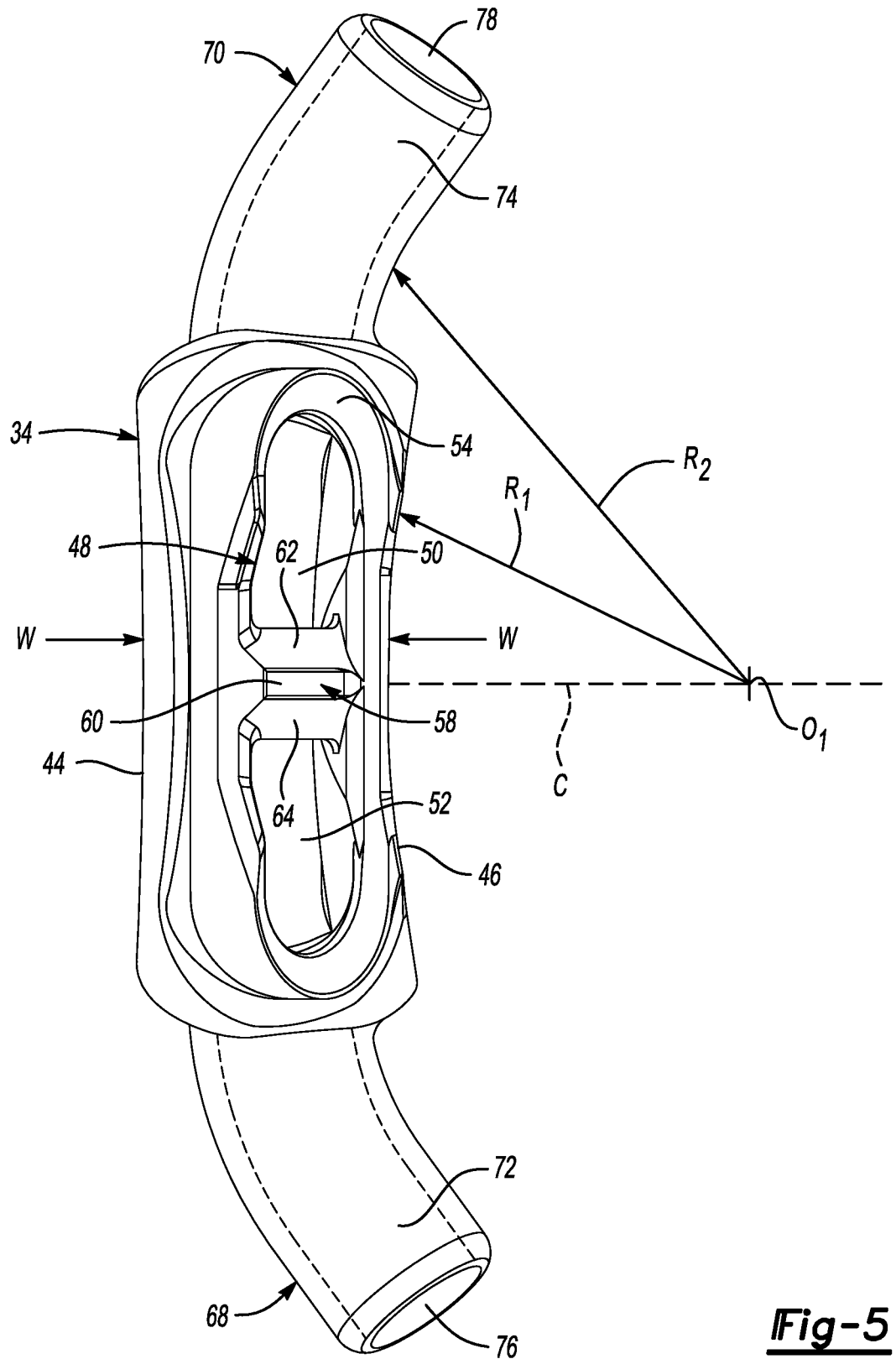
FIG. 5 is a top view of the example fitting.
Figure 6:
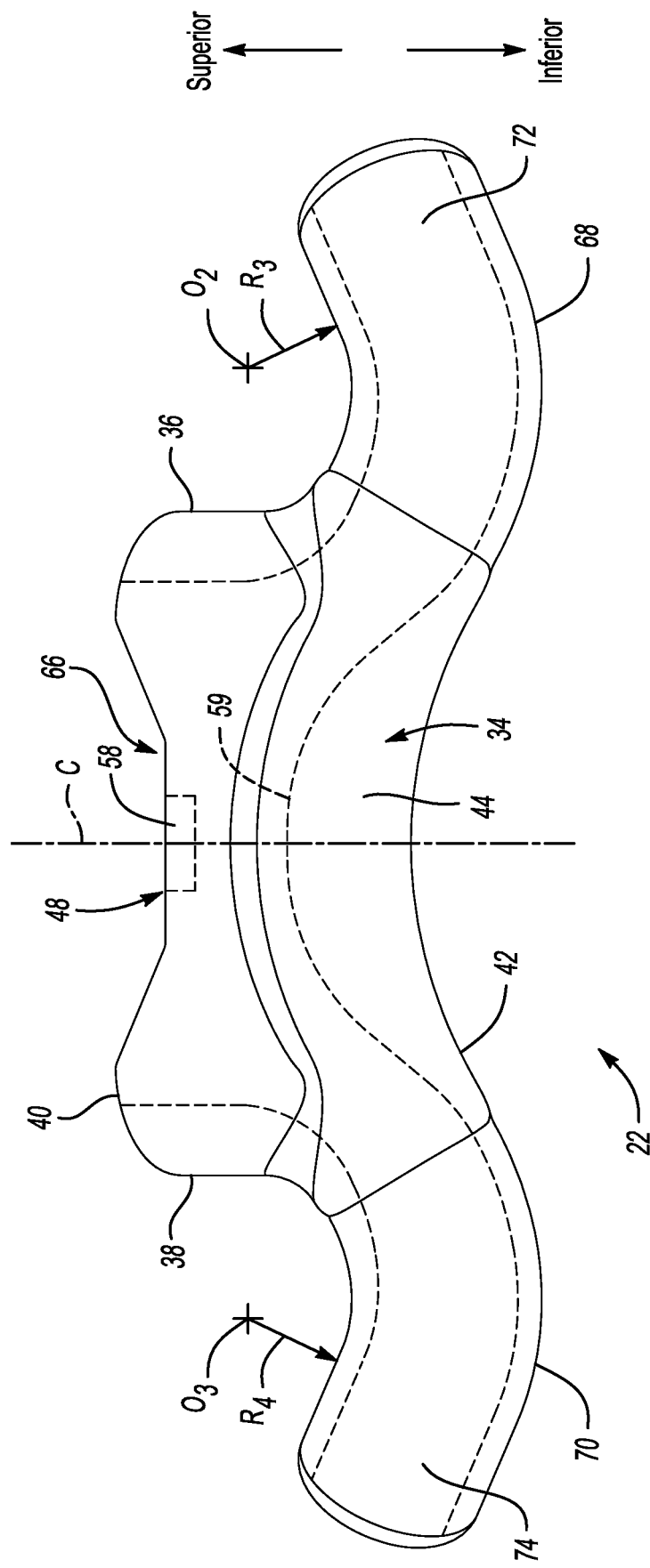
FIG. 6 is a front view of the example fitting.

With reference to FIG. 6, the inferior surface of the divider 58, in this example, is spaced-apart in a superior direction from a bottom wall 59 of an internal passageway of the fitting 22. The internal passageway(s) of the fitting 22 is represented in dashed lines in FIGS. 5 and 6. Fluid flowing to and from the first and second sections 50, 52 of the discharge port 48 can intermix in the space inferior to the divider 58 and superior to the bottom wall 59. The bottom wall 59 is convex when viewed from a superior location, and the apex of the bottom wall 59 is located on the centerline C. The curvature of the bottom wall 59 is configured to direct fluid to and from the internal passageways in the prongs located on the lateral sides of the main body portion 34 of the fitting 22, which will be discussed below. While the divider 58 assists with directing flow, in the example where there is no divider, the bottom wall 59 is used to direct fluid to and from the prongs.

Figure 7:
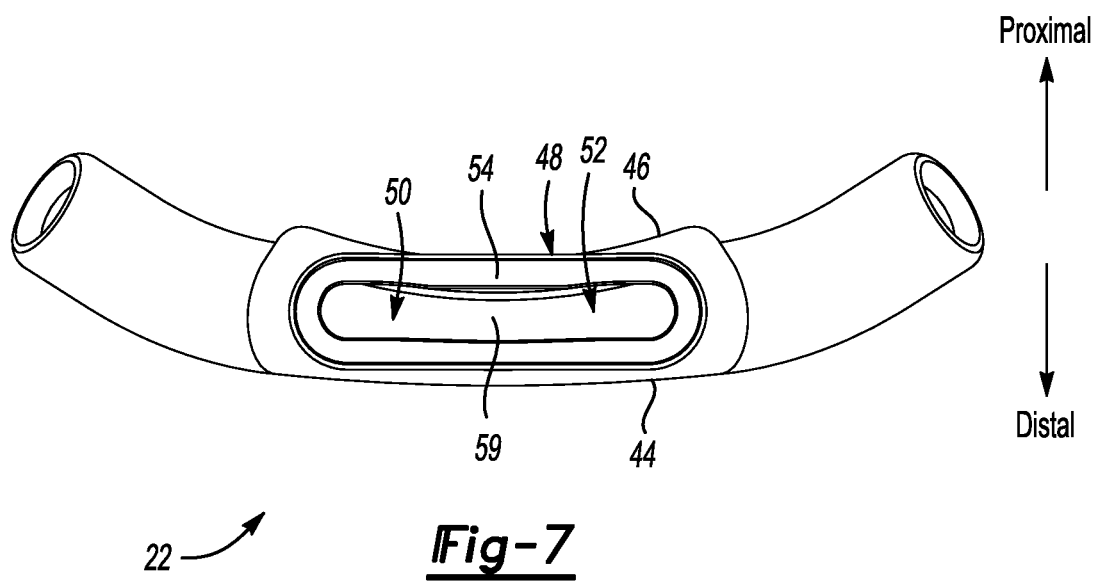
FIG. 7 is a top view of another example fitting.

The inclined wall 54 includes a notch 66 to accommodate a columella and/or tip of the nose N of the patient P. The notch 66 is formed in a distal-most portion of the inclined wall 54. The notch 66 is represented by dashed lines in FIG. 4. Because of the slope of the plane X, the notch 66 may increase comfort in some examples. The notch 66 is not present in all examples. In FIG. 7, for example, the inclined wall 54 continuously extends about its entire perimeter and does not include a notch. When the notch 66 is present, the notch 66 may be sized to correspond to a width of an average septum, columella, and/or tip of the nose.

Various aspects of this disclosure relate to preventing undesired movement of the fitting 22 relative to the nose N of the patient P during use. The nasal prongs of traditional cannulas typically resist such movement. Because the fitting 22 does not include nasal prongs, the fitting 22 includes other various features which resist movement. In one aspect of this disclosure, the proximal surface 46 of the main body portion 34 is curved. Specifically, as shown in FIG. 5, the proximal surface 46 is concave when viewed from the proximal direction. More particularly, the proximal surface 46 exhibits a contour following a constant radius $R_1$ having an origin $O_1$, which is on the centerline C and is spaced-apart from the main body portion 34 in the proximal direction. The contour of the proximal surface 46 corresponds to the contour of the philtrum of the patient P.

The fitting 22 also includes first and second prongs 68, 70 projecting laterally from the first and second lateral sides 36, 38 of the main body portion 34, respectively. The first and second prongs 68, 70 are configured to couple to respective ends of the tube 24. The first and second prongs 68, 70 are sized and shaped to resist movement of the fitting 22 during use, as will be discussed below.

In general, the first and second prongs 68, 70 include respective bores, each providing a respective internal passageway 72, 74 which ultimately leads to the discharge port 48 and is represented by dashed lines in FIG. 5. The internal passageways 72, 74 follow the contour of the first and second prongs 68, 70. The first and second prongs 68, 70 includes respective inlet ports 76, 78 leading into the respective internal passageways 72, 74. The internal passageways 72, 74 meet at a location inferior to the discharge port 48 and, when present, the divider 58.

When viewed from a top (i.e., superior) perspective, as in FIG. 5, the first and second prongs 68, 70 exhibit a curvature. Specifically, the first and second prongs 68, 70 are concave when viewed from the proximal direction. A proximal surface of the first and second prongs 68, 70 follows a constant radius $R_2$ having the origin $O_1$. The radius $R_2$ is larger than the radius $R_1$ in this example such that the prongs 68, 70 fit relative to the patient P in a manner which corresponds to the upper lip of the patient P on the lateral sides of the philtrum.

The first and second prongs 68, 70 also exhibit a curvature when viewed from another perspective. With reference to FIG. 6, the first and second prongs 68, 70 are concave when viewed from a superior location. Specifically, the first prong 68 is curved such that a superior surface of the first prong 68 follows a radius $R_3$ having an origin $O_2$ superior to the first prong 68 and spaced laterally from the first lateral side 36 of the main body portion 34. Further, the second prong 70 is curved such that a superior surface of the second prong 70 follows a radius $R_4$ having an origin $O_3$ superior to the second prong 70 and on the second lateral side 38 of the main body portion 34. The radii $R_3$, $R_4$ are the same in this example.

The first and second prongs 68, 70 are symmetrical about the centerline C. The first and second prongs 68, 70 are substantially cylindrically-shaped in cross-section such that all sides of the first and second prongs 68, 70 (i.e., not just the above-mentioned proximal and superior surfaces), and the internal passageways 72, 74, are curved according to the above-discussed curvatures.

The above-discussed orientation of the first and second prongs 68, 70 resists undesired movement of the fitting 22. In particular, the above-discussed orientation resists the tendency of the fitting 22 to flip forward, in the distal direction, as the upper lip moves during speech. Thus, the orientation keeps the discharge port 48 oriented toward the nostrils of the patient P. In part, the resistance to flipping forward is brought about by the inlet ports 76, 78 being located inferior to, or below, the discharge port 48, and namely the plane X. In this way, the tension on the fitting brought about by the tube 24, and countered by the nose N of the patient P, tends to maintain the position of the fitting 22. Specifically, the position of the fitting 22 is more stable and is not easily altered during speech or other activities.

When worn by the patient, the discharge port 48 is configured to be situated inferior to (i.e., vertically beneath) the nose N of the patient P, and specifically such that the first section 50 is inferior to a right nostril (from the patient's perspective) of the patient P and the second section 52 is configured to be situated inferior to a left nostril of the patient P. Further, the divider 58 and notch 66 are configured to be situated inferior to a columella and/or tip of the nose N of the patient P.

The fitting 22 is integrally formed as a one-piece structure in one example. In particular, the fitting 22 is provided by an integrally molded piece of plastic. In some embodiments, the fitting 22 is made entirely of silicone, or another soft elastomer. The fitting 22 may be made of same material as tube 24 or a different material. While above the fitting 22 was described as being separate from the tube 24, the fitting 22 could be formed integrally with the tube 24.

Because the fitting 22 does not include nostril prongs and no portion of the fitting 22 enters the nostrils of the patient P, patient comfort is dramatically increased relative to traditional nasal cannula and nasal pillow designs. However, because the discharge port of the fitting 22 is further away from the nostrils of the patient P than in cannulas with nostril prongs, for example, various operating parameters and settings of the oxygen supply 14 are adjusted in this disclosure. In particular, in an aspect of this disclosure, the sensitivity of the sensor 18 is increased. In particular, the controller 20 is configured to identify, based on the information (e.g., signal) from the sensor 18, an exhale or inhale of the patient P at a lower change in pressure than in traditional nasal cannulas. In an example, the controller 20 instructs the blower 16 to deliver a flow of fluid (e.g., oxygen) when the sensor 18 indicates a change in pressure as low as 0.05 cm $H_2O$. In a further example, the controller 20 instructs the blower 16 to deliver a flow of fluid (e.g., oxygen) when the sensor 18 indicates a change in pressure within a range of as 0.05 cm $H_2O$ and 0.3 cm $H_2O$. Such pressure changes are readily detected in part due to the inclined wall 54, discussed above. Further, to account for potential losses due to the space between the fitting 22 and the nose N, the blower 16 could deliver fluid at a higher rate than in systems with traditional nasal cannulas.

It should be understood that terms such as "generally," "substantially," and "about" are not intended to be boundaryless terms, and should be interpreted consistent with the way one skilled in the art would interpret those terms. Further, various directional terms, such as "superior," "inferior," "distal," "proximal," etc., have been used herein and labeled in some figures for ease of reference. These directional terms are used with reference to the normal operational Although the different examples have the specific components shown in the illustrations, embodiments of this disclosure are not limited to those particular combinations. It is possible to use some of the components or features from one of the examples in combination with features or components from another one of the examples. In addition, the various figures accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A nasal cannula for an oxygen delivery system, comprising:
   a tube configured to connect to an oxygen supply; and
   a fitting configured to connect to the tube, wherein the fitting includes a single discharge port having a first section configured to be situated inferior to a first nostril of a user and a second section configured to be situated inferior to a second nostril of the user, wherein the fitting does not include nostril prongs, wherein the fitting includes a main body portion, a first prong projecting laterally from a first side of the main body portion, and a second prong projecting laterally from a second side of the main body portion, wherein the first and second prongs are curved such that superior surfaces of the first and second prongs are concave when viewed from a proximal location; wherein a proximal surface of the main body portion is concave when viewed from a superior location;
   and wherein the superior surface of the first prong is curved following a constant radius having a first origin superior to the first prong and on the first side of the main body portion, and the superior surface of the second prong is curved following a constant radius having a second origin superior to the second prong and on the second side of the main body portion.

2. The nasal cannula as recited in claim 1, wherein the first and second prongs are curved such that proximal surfaces of the first and second prongs are concave when viewed from a superior location.

3. The nasal cannula as recited in claim 1, wherein the fitting includes a divider located along a centerline of the fitting separating the first section and the second section.

4. The nasal cannula as recited in claim 1, wherein the fitting does not include a divider such that the first section of the discharge port blends directly into the second section of the discharge port.

5. The nasal cannula as recited in claim 1, wherein:
   the fitting includes an inclined wall projecting from an apex of a superior surface of the fitting,
   the apex circumscribes substantially the entire discharge port, and
   the inclined wall projects from the apex in a direction toward a center of the discharge port and in an inferior direction.

6. The nasal cannula as recited in claim 5, wherein, when the fitting is positioned to provide gas to the first and second nostrils of the user, the fitting is configured to be spaced-apart from a nose of the user.

7. The nasal cannula as recited in claim 6, wherein a distal-most portion of the inclined wall is notched.

8. The nasal cannula as recited in claim 1, wherein the main body portion includes an area where first and second internal passageways meet at a location spaced-apart from the discharge port in an inferior direction.

9. The nasal cannula as recited in claim 1, wherein:
   a first portion of the tube is configured to fit over the first prong, and
   a second portion of the tube is configured to fit over the second prong.

10. The nasal cannula as recited in claim 1, wherein the fitting is integrally formed as a one-piece structure.

11. The nasal cannula as recited in claim 10, wherein the fitting is provided by an integrally molded piece of plastic.

12. The nasal cannula as recited in claim 1, wherein first and second ports defined by a respective one of the first and second prongs are inferior to the discharge port.

13. The nasal cannula as recited in claim 1, wherein, when the fitting is positioned to provide gas to the first and second nostrils of the user, the inferior direction is a generally downward direction facing towards a mouth of the user, the superior direction is a generally upward direction opposite the inferior direction, the proximal direction is generally toward the user, and the distal direction is generally away from the user.

14. The nasal cannula as recited in claim 1, wherein the first and second prongs are oriented to resist undesired movement of the fitting and to keep the discharge port oriented toward the first and second nostrils of the user.

15. The nasal cannula as recited in claim 1, wherein the discharge port is configured to deliver oxygen to the user and is also configured to collect an exhale of the user.

16. The nasal cannula as recited in claim 1, wherein the fitting does not surround a tip of the nose of the user.

17. A system, comprising:
   a nasal cannula including a tube and a fitting connected to the tube, wherein the fitting includes a discharge port, wherein the fitting does not include nostril prongs, and wherein the fitting includes an inclined wall adjacent the discharge port configured to collect an exhale of a patient, wherein the fitting includes a main body portion, a first prong projecting laterally from a first side of the main body portion, and a second prong projecting laterally from a second side of the main body portion, wherein the first and second prongs are curved such that superior surfaces of the first and second prongs are concave when viewed from a proximal location and such that the first and second prongs initially project from the main body portion in an inferior direction and, at a point between an end of the first and second prongs and the main body portion, the first and second prongs project in a superior direction; and
   an oxygen supply connected to the tube and including a blower and a sensor, wherein the blower is configured to deliver oxygen to the tube.

18. The system as recited in claim 17, wherein:
   the first and second prongs are curved such that proximal surfaces of the first and second prongs are concave when viewed from a superior location,
   first and second ports defined by a respective one of the first and second prongs are inferior to the discharge port, and
   the discharge port is configured to deliver oxygen to the user and is also configured to collect an exhale of the user.

* * * * *